United States Patent [19]

Koike

[11] Patent Number: 5,401,667
[45] Date of Patent: Mar. 28, 1995

[54] IMMUNOCHROMATOGRAPHIC ASSAY SYSTEM AND METHOD

[75] Inventor: Tetsuo Koike, Matsubara, Japan

[73] Assignee: Rohto Pharmaceutical Co., Ltd., Osaka, Japan

[21] Appl. No.: 858,823

[22] Filed: Mar. 27, 1992

[30] Foreign Application Priority Data

Mar. 28, 1991 [JP] Japan .................. 3-064504

[51] Int. Cl.$^6$ .................. G01N 33/50; G01N 33/569; G01N 33/544; G01N 33/551
[52] U.S. Cl. ........................... 436/514; 422/57; 422/58; 422/56; 436/530; 436/521; 435/7.1
[58] Field of Search ............... 436/514, 530, 810, 587, 436/528; 422/56, 57, 58; 435/910, 7.1

[56] References Cited

U.S. PATENT DOCUMENTS

| | | |
|---|---|---|
| 4,861,711 | 8/1989 | Friesen et al. ............ 436/7 |
| 4,916,056 | 4/1988 | Brown et al. |
| 4,960,691 | 10/1990 | Gordon et al. ............ 435/6 |
| 5,006,474 | 4/1991 | Horstman et al. ......... 422/56 |
| 5,075,078 | 12/1991 | Osikowicz et al. ........ 422/56 |
| 5,120,643 | 1/1992 | Ching et al. ............ 435/7.92 |
| 5,141,875 | 8/1992 | Kelton et al. |
| 5,147,608 | 9/1992 | Grenner ................ 422/56 |
| 5,202,268 | 4/1993 | Kuhn et al. ............. 422/56 |

FOREIGN PATENT DOCUMENTS

| | | | |
|---|---|---|---|
| 0299428 | 1/1988 | European Pat. Off. | ........ 422/58 |
| 0260965 | 3/1988 | European Pat. Off. | |
| 0262328 | 4/1988 | European Pat. Off. | |

*Primary Examiner*—Christine M. Nucker
*Assistant Examiner*—Chris Dubrule
*Attorney, Agent, or Firm*—Bradford E. Kile; Ruffin B. Cordell; Michael J. McKeon

[57] ABSTRACT

A method for detecting the presence of a specific analyte in solution comprising the steps of affixing to a chromatographic medium a first antibody which binds with specificity to the analyte in a pattern which forms a pre-determined geometric symbol or symbols consisting of a plurality of line segments; partially blocking or obstructing the expected passage of a moving phase or solvent through the symbol; reacting the solution to a marker-second antibody complex which binds with specificity to the analyte to form analyte-marker-second antibody complexes in the presence of the analyte; eluting the solution containing any analyte-marker-second antibody complex through the partially blocked or obstructed medium; and observing the substantially complete formation, or lack thereof, of the predetermined geometric symbol or symbols by means of the marker.

16 Claims, 3 Drawing Sheets

| HCG (mIU/ml) | + | + | + | + |
|---|---|---|---|---|
| 0 | — | — | — | — |
| 25 | — | + | + | + |
| 50 | — | + | + | + |
| 100 | — | + | + | + |

FIG. 3

| HCG (mIU/ml) | + | + | + | + |
|---|---|---|---|---|
| 0 | — | — | — | — |
| 25 | — | + | + | + |
| 50 | — | + | + | + |
| 100 | — | + | + | + |

FIG. 4

IMMUNOCHROMATOGRAPHIC ASSAY SYSTEM AND METHOD

TECHNICAL FIELD

The present invention relates to an improved method of determining, by the appearance of a symbol on a chromatographic medium, whether or not a substance of interest or clinical significance is present in a particular solution, by means of an immunochromatographic method which combines the so-called sandwich immunoassay method with chromatography used for separation of reaction products from unreacted components (typically called "BF separation"). The method of this invention is to be used in the field of in vitro diagnosis, and particularly in the field of diagnosis by visual determination; since the results to be judged are indicated clearly by predetermined symbols, even a person with no particular training can easily judge the diagnostic results. More particularly, the invention relates to a method for improving the clarity and completeness of appearance of the predetermined symbol so the presence of a positive or negative result can be more easily and accurately judged.

The invention also relates to a diagnostic system by which the presence or absence of an analyte can be determined by chromatographic means.

BACKGROUND OF THE INVENTION

Immunochromatographic methods have been used as diagnostic means for determining the presence, or absence, of substances of interest or of clinical significance. Generally, these substances are referred to as "analytes" which can consist of antibodies, antigens or other ligands. By taking advantage of the highly specific affinity of known antibodies for specific analytes, immunochromatography is a highly sensitive method for determining the presence or absence of an analyte. Preferably, such methods are simple and easy to judge so that they can be utilized by a broad group of persons, including those with little or no technical expertise.

These methods rely on certain basic known principles. A "first" antibody which binds with specificity to the analyte is affixed near the center of a typically rectangular chromatography medium, e.g. filter paper. A "second" antibody, namely an antibody different from the first antibody yet which also binds with specificity to the analyte, is prepared separately and bound to a detectable marker substance to prepare a marker—second antibody complex. When this second antibody is mixed with a liquid specimen thought to contain a particular analyte, a conjugate of (marker)-(second antibody)-(analyte) is formed. If a liquid specimen containing this conjugate is placed in contact with the edge of the chromatography medium and developed, the conjugate will move gradually in the direction of development and reach the affixed first antibody, thus forming a complex of (marker)-(second antibody)-(analyte)-(first antibody). (In this specification and the following claims, the term "developer" refers to the solvent or moving phase. The direction of development is the direction of the movement of the moving phase.) Because the marker is detectable, the presence of the (marker)-(second antibody)-(analyte)-(first antibody) can be detected. In certain systems, the marker can be detected by the naked eye, i.e. by means of color contrasting with the chromatographic medium. Therefore, a colored mark or the like will be left by the marker at the site at which the first antibody was affixed, (said affixation typically done in the form of a predetermined geometric symbol) and thereby it is possible to easily confirm the presence (or absence) of the analyte.

At present, many such in vitro diagnostic kits based on immunochromatography are known and available commercially, and in most of these, the method of determining the result is based on detecting the presence or absence of a spot or line at the site of the first antibody. When results are determined in this way, it is possible that the positive or negative result may be ambiguous depending on the intensity of the tinting. To solve this problem, a (+) or (−) indicator is used to simplify the judging of results by the user has been proposed, for example, in Japanese Patent Application Public Disclosure No. Sho 64-32169.

In this method, a symbol (+) is placed on the chromatography medium and the first antibody is bound to one line, e.g. the vertical line, of the symbol, while a sample of the analyte or antibody to the second antibody is bound to the horizontal line. If the liquid specimen does not contain the analyte, a complex of (marker)-(second antibody)-(analyte) or (marker)-(second antibody)-(antibody to the second antibody) is formed only on the horizontal line, and the symbol (−) appears as the result. The appearance of this symbol acts as a positive control. If the analyte specimen does contain the analyte, one of the aforesaid complexes will be formed on the horizontal line of the (+) symbol, while a complex of (marker)-(second antibody)-(analyte)-(first antibody) is formed on the vertical line, so the symbol (+) appears as the result. With this method, even in the event that the sample of the analyte and/or the second antibody bound to the marker affixed to the chromatography medium were to become inactive for some reason, or if a major error in handling would occur, the horizontal line will not appear, so it is possible to determine whether the diagnostic test was performed correctly or not. In this manner, this (+) or (−) indicator method has a great advantage in that the validity of the diagnostic test can be verified. Other predetermined geometric symbols can also be used.

However, this method has a major drawback in that it is difficult to get a clear color indication in any line drawn parallel or substantially parallel to the direction of development, for example, the vertical line of the (+) symbol, or portions of "Y" or "N" symbols for the following reason.

If the liquid specimen or solvent potentially containing the analyte having the conjugate of (marker)-(second antibody)-(analyte) reaches the lower edge of the vertical line of the (+) symbol or the vertical lines of "Y" or ,"N" symbols, it reacts with the first antibody forming the complex of (marker)-(second antibody)-(analyte)-(first antibody). However, the complex formed on the lower portion of these lines impedes the further migration of the solvent so the liquid specimen does not come into contact with the portion of the affixed first antibody on the upper part or downstream portion of the vertical indicator lines. As is evident from the FIGS. 1–5, this may result in only small portions of the vertical lines positioned below the other indicator lines reacting or only the top edge and bottom edge of the vertical line reacting, so true (+), "Y" or "N" symbols are not formed correctly. This result occurs if different geometric symbols are used, i.e. only a partial development of the symbol is effected because of the blocking effect of the analyte-marker-second antibody-first antibody complex.

For these reasons, the diagnostic kits presently sold based on the (+) or (−) indicator method must be sold with instructions which indicate that even an incomplete (+) symbol with a missing upper edge or central portion should be considered to be positive. This leads to some confusion, particularly among relatively unskilled technicians or totally untrained consumers with respect to "interpreting" the results, and leads itself to possible mistakes.

In order to overcome the above drawbacks, the following improvements have been proposed.

(1) The line parallel to the direction of development (the vertical line) is pre-printed with the same color as the marker, so that a "+" is indicated when a reaction occurs in the line perpendicular to the direction of development (the horizontal line). An example of this is the commercially available C.A.R.D.± ®O.S ™ kit made by Pacific Biotech, Inc.

(2) In another method, the horizontal and vertical lines are made to be oblique with respect to the direction of development. An example is the commercially available TESTPACK+Plus ™ kit manufactured by Abbott Laboratories, Inc., Abbott Park, Ill.

However, these methods have various drawbacks and are not satisfactory. With method (1), the means of verifying the validity of the diagnostic test (the positive control), namely the method of binding a sample of the analyte to the horizontal line, cannot be employed, so the reliability of the diagnostic test cannot be guaranteed. With method (2), the reaction merely occurs in a skewed "V" shape, so the above drawbacks are not overcome and a true (+) symbol will still not be formed correctly and completely. Therefore, a method which ensures the complete development of the pre-determined symbol is desirable, particularly because complete development will greatly improve the reliability and accuracy of the method.

In light of the above situation, the inventor of this invention made the surprising discovery—as a result of varied efforts at development of a method whereby indicator symbols (a "+", "−", "Y", "N" or some other predetermined symbol) will appear substantially completely and clearly—that by removing a portion of the chromatographic medium, or otherwise partially blocking or obstructing the path of the solvent's movement downstream, complete reaction of the predetermined geometric symbol will occur. As a result of further research, the inventor confirmed that in addition to the widely used (+) or (−) indicators other symbols, e.g. the letters "Y" and "N" which indicate YES or NO, can be utilized with similar clarity.

SUMMARY OF THE INVENTION

The present invention contemplates a method for detecting the presence of an analyte in solution which comprises the steps of affixing to a chromatographic medium a first antibody which binds with specificity to said analyte in the form of a predetermined geometric symbol or symbols. A solution potentially containing the said analyte is reacted with marked second antibody which is also specific to said analyte to form an analyte-marker-second antibody complex in the presence of the analyte. The solution containing the analyte-marker-second antibody complex is eluted through the chromatographic medium and passes through the predetermined geometric symbol or symbols. A portion or portions of the chromatographic medium have been removed, or passage of the moving phase or solvent through said symbol or symbols on the chromatographic medium has otherwise been partially blocked or obstructed. As the analyte-marker-second antibody complex solution passes through the chromatographic medium, it forms a first antibody-analyte-marker-second antibody complex. The result is the ability to observe a substantially complete formation, or lack thereof, of the predetermined geometric symbol or symbols by means of the marker which has been bound to the second antibody and forms part of any first antibody-analyte-marker-second antibody complex.

In preferred embodiments, the partial blockage or obstruction of the flow of the solvent is positioned immediately upstream of the predetermined geometric symbol, positioned within the predetermined geometric symbols, or positioned both upstream and within said predetermined geometric symbols. In particularly preferred embodiments, the partial blockage or obstruction of the flow of the solvent is formed by means of "notching", cutting or punching holes or otherwise cutting a form in said medium or by means of physically affixing a hydrophilic blocking agent to said medium. A preferred hydrophilic blocking agent is a hydrophilic polymer, and a particularly preferred polymer is an oil-based ink. The notches, holes, cuts or the hydrophilic blocking agent can be positioned on the lateral edges of said medium and can be in the form of rectangles, half-circles and/or triangles.

In a preferred embodiment, the marker is taken from the group consisting of colloidal gold particles, colored latex and insoluble dye polymers. A preferred medium is taken from the group comprising glass filters, nitrocellulose and/or nylon. The antibody can be applied by a number of methods; preferred methods include direct printing of an aqueous solution or printing with latex to which the first antibody is bonded.

In a particularly preferred embodiment, the marker-second antibody complex is affixed to the chromatographic medium upstream from the affixed first antibody. Therefore, when the solution which may contain the analyte passes through the chromatographic medium, it reacts first with the bound marker-second antibody complex to form an analyte-marker-second antibody complex prior to reaching the predetermined geometric symbol. If the analyte is present, a first antibody-analyte-marker-second antibody complex will form and all or substantially all of the predetermined geometric symbol can be observed.

The invention also contemplates an immunochromatographic diagnostic system for detecting the presence or absence of a specific analyte. The system consists of a chromatographic medium to which a first antibody specific to the analyte to be detected has been affixed in the form of a predetermined geometric symbol. The downstream flow of a solvent containing analyte-marker-second antibody complex specific for said analyte is partially blocked or obstructed at one or several points on the medium. The blockage or obstruction can be formed by many forms of barrier means such as physically removing part of the medium by a notch or notches, holes or otherwise on the chromatographic medium or by the placement of hydrophilic blocking agents on said medium or by other suitable means. In a particularly preferred embodiment, the marker-second antibody complex specific for the analyte is affixed upstream of the predetermined geometric symbol or symbols, so the elution of the solution which may contain the analyte reacts first with the marker-second antibody complex to form an analyte-marker-second antibody complex before reaching the predetermined geometric symbol or symbols.

BRIEF DESCRIPTION OF THE DRAWING

FIG. 3: Schematic diagram illustrating the results of (+) or (−) indicators on control and notched chromatography strips and strips to which the second antibodies had been previously bound FIG. 4: Schematic diagram illustrating the results of (+) or (−) indicators on chromatography control strips and strips to which oil-based ink is applied and to which the second antibodies had been previously bound.

DETAILED DESCRIPTION OF THE PREFERRED EMBODIMENT

A. GENERAL

Figure 1:
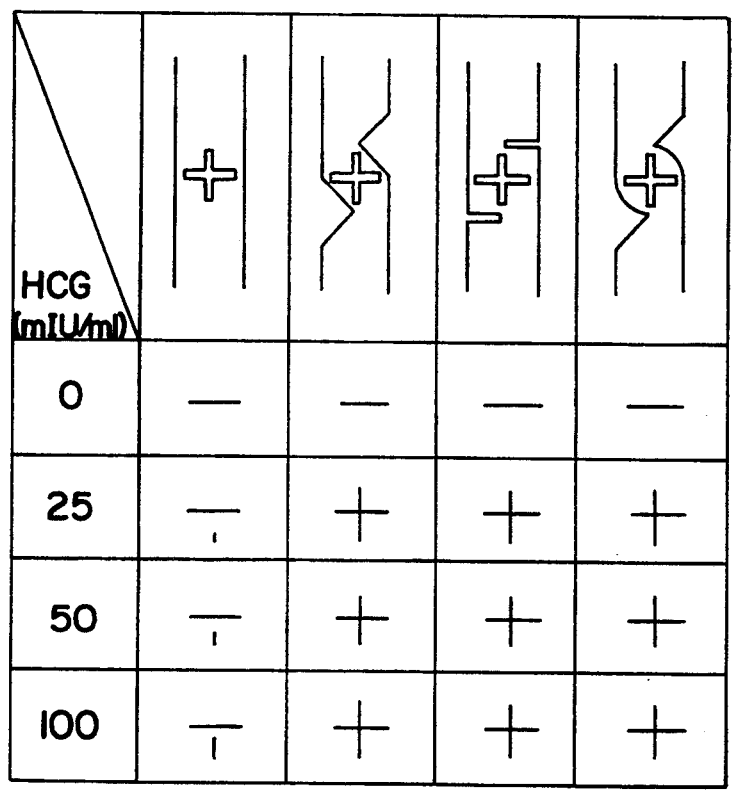
FIG. 1: Schematic diagram illustrating the results of (+) or (−) indicators on control and notched chromatography strips.

In this specification, a liquid specimen refers to any aqueous solution, but particularly to bodily fluids such as blood, urine, or suitable dilute solutions of such, which contain, or are suspected to contain, the substance sought to be detected, i.e. the analyte. The analyte generally refers to a substance which contributes to an immunoreaction, particularly an antigenic substance which is subject to detection in various types of diagnosis, namely haptens and antibodies. In the present invention, examples of antigenic substances applied as the subject of detection include thyroid-stimulating hormone (TSH), follicle-stimulating hormone (FSH), human chorionic gonadotropin (HCG) and luteinizing hormone (LH). The haptens applied as the subject of detection in the present invention include estrone, estradiol, testosterone, progesterone, and their ester derivatives.

The chromatography medium may be a carrier normally used in chromatography, such as glass filters, nitrocellulose, nylon, filter paper, or the like. As the marker, colloidal gold particles, colored latex, insoluble dye polymers, or other colored substance is preferable, but a colorless substance which becomes colored when put into contact with a coloring reagent may also be used.

In the present invention, means of partially blocking or obstructing the passage of the developer or moving phase refers to a means of disrupting the normal flow of developer made up of the liquid specimen which contains the second antibody. Normally, the developer will move at a relatively even rate through the medium, with little difference in the rate of passage from lateral edge to lateral edge of the medium. Effective but not exclusive blockage or obstruction methods include removing a portion or portions of the medium by notching, punching a hole, cutting or by other means, or the application of a hydrophobic substance to the medium, or by the placement of barrier means. The site or sites at which this means of obstruction is provided can vary, being preferably upstream of the site at which the first antibody is affixed; locating the blockage means on the lateral edges of the chromatography medium is particularly preferable. Moreover, there are cases in which the provision of a downstream site or sites as well is preferable.

There are no particular limitations as to the shape of the portion of the medium to be removed, as various shapes such as rectangles, half-circles, triangles, and rough triangles are all effective. Consequently, when applying a hydrophobic substance or other barrier means, various shapes can be employed.

As the hydrophobic substance, any substance which adheres to the chromatography medium may be used, including hydrophilic polymers or the like which may be hydrophilic when applied but then become hydrophobic during subsequent polymerization or the like. A preferred specific example is oil-based ink.

There are many methods well known to one of ordinary skill in the art of affixing the first antibody to the chromatography medium. Namely, both direct and indirect methods of affixing the antibody reagent are conceivable. Direct methods include (1) a method of using bromine cyanide, glutaraldehyde, and carbodiimide to affix the antibodies with covalent bonds (the covalent bond method) and (2) a method of affixing antibodies using physical adsorption (the non-covalent bond method). Indirect methods include a method of binding the antibody reagent to latex particles or other insoluble particles, and then affixing the particles, so either covalent bond methods or non-covalent bond methods can be used. In this case, the size of the latex particles must be selected as an appropriate size such that they will adhere sufficiently to the chromatography medium but not move during chromatography development.

The marker second antibody may be prepared by mixing a freeze-dried extract with the liquid specimen at the time when the diagnostic test is to be performed. Alternately, non-woven fabric or other porous polymer may be impregnated with this marker second antibody, freeze-dried, and then secured to a site upstream of the site on the chromatography medium at which the first antibody is affixed. In this case, the person performing the test need only apply the liquid specimen to the end of the chromatography medium, eliminating the work of mixing the marker second antibody and the liquid specimen. Namely, the marker second antibody, secured in the direction of development of the liquid specimen, is eluted by the liquid specimen during development, thus forming the conjugate (marker)-(second antibody)-(analyte) which is transported to the affixed first antibody.

While the present invention is described above based on the sandwich method of [first antibody]-[analyte (antigen)]-[second antibody], persons skilled in the art can readily understand that the present invention can also be implemented in a system made up of [antigen]-[analyte (antibody)]-[antibody to the analyte]. Therefore, the present invention is not limited to the case in which the analyte is an antigen, but also includes the case in which it is an antibody, so the present invention may be embodied in this case as if each instance of antibody were replaced with antigen and vice versa.

B. EXPERIMENTAL (1) Preparation of solid-phase latex A

A commercial latex emulsion (N-450, made by Sekisui Chemical Co., Ltd.) is diluted to a solid content concentration of 0.6 wt. % in phosphate-buffered saline (PBS) solution, 1 ml of which is collected in an Eppendorf micro-centrifuge with 1 ml of rabbit antibody to human chorionic gonadotropin (hCG) (600 $\mu$g/ml concentration) and dissolved by shaking for 2 hours at room temperature to bind the rabbit antibody to the latex particles. The latex particles are then centrifuged and washed three times in PBS containing a 0.1 wt % concentration of bovine serum albumin (BSA) and then suspended again in PBS to give a final volume of 2 ml, thereby preparing solid-phase latex A.

(2) Preparation of solid-phase latex B

Solid-phase latex B is prepared in the same manner as solid-phase latex A, but with hCG (made by Teikoku Hormone Mfg. Co., Ltd.) used instead of the rabbit anti-hCG antibody.

(3) Preparation of colloidal gold particles

After boiling 200 ml of a 0.01 wt. % aqueous solution of gold chloride, a 1 wt. % aqueous solution of sodium citrate is added and the mixture boiled while heating until the color of the solution changes from a light yellow to purple or red, thus preparing a disperse solution of colloidal gold with an average particle size of 0.03 $\mu$m.

(4) Preparation of colloidal gold marker antibodies

A solution of potassium carbonate is added to the above disperse solution of colloidal gold which has a gold concentration of 0.01 wt. % until a pH of 7.6 is reached. To this is added a quantity of monoclonal antibodies to hCG (obtained by means of the well-known hybridoma method, prepared from mouse ascites or cell-culture supernate) sufficient to obtain a proportion of 10 $\mu$g per ml of disperse solution of colloidal gold, of which 10 ml is added to 0.1 ml of 30 wt. % BSA. The mixture is centrifuged, the supernate removed, and PBS containing 0.1 wt. % BSA is used to centrifuge and wash the mixture three times. The mixture is dispersed back into 10 ml of the aforesaid PBS, and 0.25 ml is decanted into a test tube (method A).

A 12×12 mm square of Benrize ® nonwoven fabric (made by Asahi Chemical Industry Co., Ltd.) is impregnated with 0.25 ml of a disperse solution of the aforesaid colloidal gold marker antibodies and freeze-dried to prepare non-woven cloth containing a colloidal gold antibody (method B).

(5) Preparation of chromatography strip A

A commercial glass filter (GC-50, made by Toyo Roshi Co.) is cut into 12×60 mm thin strips which are placed upon glass plates (TLC plates) and secured with tape for ease of handling. At a site 30 mm from the bottom edge of the strips, an Acurajetter ™ liquid jet device (made by Nordson Co.) and an XY table aerostage (made by THK Co.) are used to jet-print the solid-phase latex A at a rate of 0.1 $\mu$m/mm for a length of 10 mm in the direction of development, namely the lengthwise direction of the strip. After drying, solid-phase latex B is jet-printed at a rate of 0.1 $\mu$m/mm for a length of 10 mm perpendicular to the direction of development, namely across the short direction of the strip, thereby printing a "+".

(6) Preparation of chromatography strip B

Portions of the aforesaid chromatography strip A are cut between 10 mm and 15 mm from the bottom edge, and these portions are connected by staples with the aforesaid non-woven cloth containing a colloidal gold marker antibody to give a strip which again has an overall length of 60 mm.

(7) Preparation of chromatography strip C

The aforesaid commercial glass filter is made into 12×80 mm thin strips which are secured to glass plates (TLC plates). The aforesaid printing device is used to print a "Y" with 0.1 $\mu$l/mm of solid-phase latex A at a site 30 mm from the bottom of the strip, and to print an "N" with 0.1 $\mu$l/mm of solid-phase latex B at a site 50 mm from the bottom of the strip.

(8) Preparation of an hCG-containing specimen

An injectable type of hCG, "Gonatropin 5000" (made by Teikoku Hormone Mfg. Co., Ltd.), is diluted with PBS containing 0.1 wt. % BSA to prepare hCG-containing specimens with hCG concentrations of 25 mIU, 50 mIU and 100 mIU per ml.

(9) Study of notches for "+" and "−" indicators in two-step immunochromatography Various notches are cut around the reaction site (the site at which the first antibody is affixed with an artisan's knife) on the aforesaid chromatography strips A (see FIG. 1), so that the mixture of the liquid specimen and colloidal gold marker antibodies cannot develop in the notched portions.

One 500 $\mu$l portion of each of the aforesaid hCG-containing specimens or a blank of 500 $\mu$l of PBS containing 0.1 wt. % BSA is added each to a test tube containing the aforesaid colloidal gold marker antibodies and stirred. The mixtures thus obtained are allowed to impregnate only the lower 5 mm of the aforesaid chromatography strips A with various notches cut in, or a control chromatography strip A with no notches, and development of said liquid specimen is allowed to occur. After 5 minutes have passed, the "+" or "−38 indicators in the reaction sites are compared visually.

The results of the indicator appearances and shapes are illustrated in FIG. 1.

(10) Study of applying oil-based ink for "+" or "−" indicators in two-step immunochromatography Commercial oil-based ink (correction fluid, made by Zebra Co., Ltd.) is applied in various patterns around the reaction site on the aforesaid chromatography strips A (see FIG. 2), and after drying, the same mixtures of liquid specimen and colloidal gold marker antibodies as in (9) above are allowed to impregnate the strips, and after 5 minutes of development, the "+" or "−" indicators in the reaction sites are compared visually.

Figure 2:
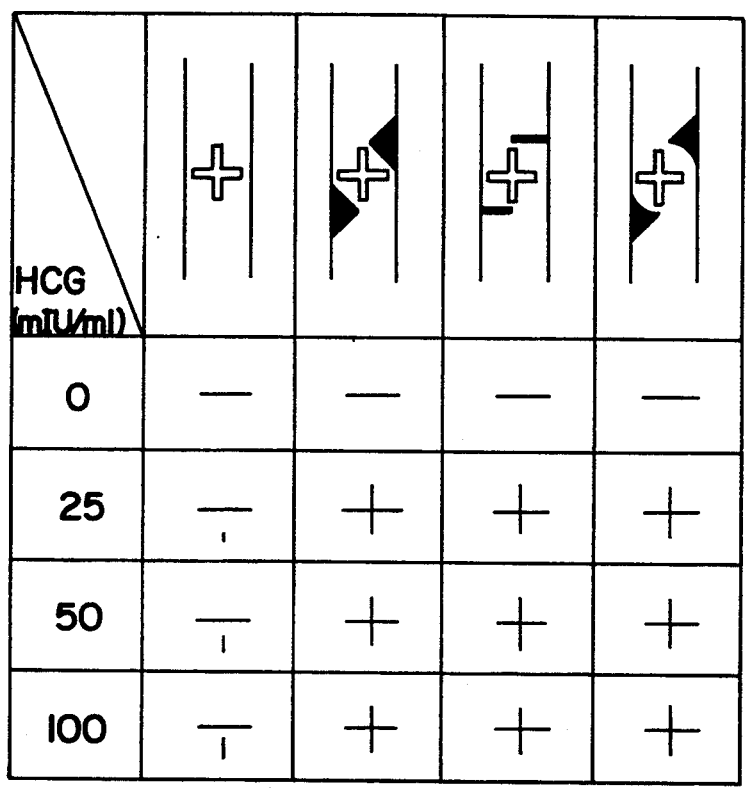
FIG. 2: Schematic diagram illustrating the results of (+) or (−) indicators on chromatography control strips and strips to which oil-based ink is applied.

The results of the indicator appearances and shapes are illustrated in FIG. 2.

(11) Study of notches for "+" and "−" indicators in one-step immunochromatography Various notches are cut as in (9) above on the aforesaid immunochromatography strips B (see FIG. 3), and 500 $\mu$l portions of each of the hCG-containing specimens as in (9) above or a blank of PBS containing 0.1 wt. % BSA in test tubes are allowed to impregnate only the lower 5 mm of the strips, and after 5 minutes of development, the "+" or "−" indicators in the reaction sites are compared visually.

The results of the indicator appearances and shapes are illustrated FIG. 3.

(12) Study of applying oil-based ink for "+" and "−" indicators in one-step immunochromatography Commercial oil-based ink is applied as in (10) above to the aforesaid chromatography strips B, and after drying, the same liquid specimens as in (11) above are allowed to impregnate only the lower 5 mm of the strips, and after 5 minutes of development, the "+" or "—" indicators in the reaction sites are compared visually.

The results of the indicator appearances and shapes are illustrated in FIG. 4.

(13) Study of notches for "Y" and "N" indicators in two-step immunochromatography Notches are cut around the sites at which the "Y" or "N" indicators are printed on the aforesaid immunochromatography strips C (see FIG. 5), and 500 μl portions of each of the hCG-containing specimens as in (9) above or a blank of PBS containing 0.1 wt. % BSA in test tubes are allowed to impregnate only the lower 5 mm of the strips, and after 10 minutes of development, the "Y" or "N" indicators in the reaction sites are compared visually.

Figure 5:
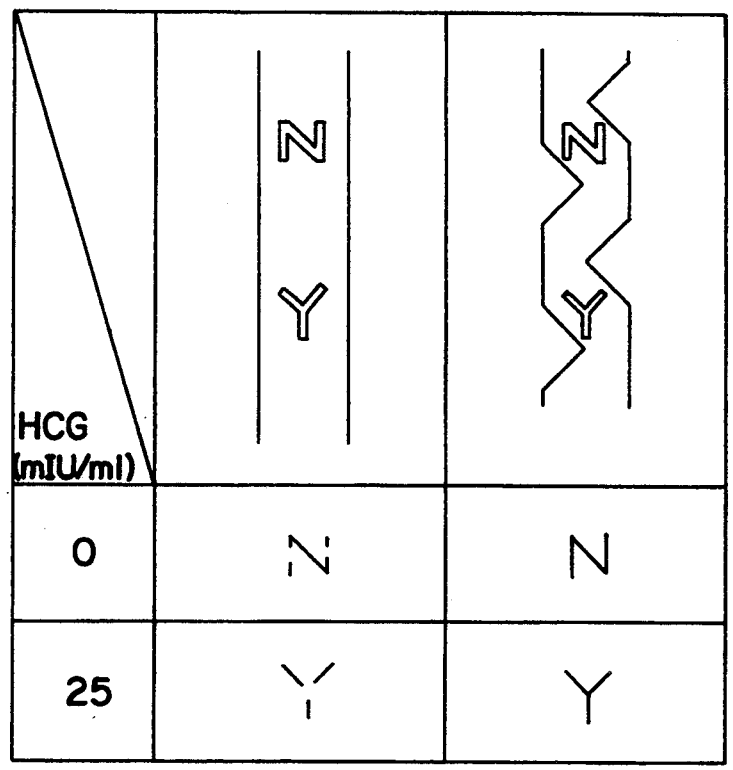
FIG. 5: Schematic diagram illustrating the results of (Y) or (N) indicators on control and notched chromatography strips.

The results of the indicator appearances and shapes are illustrated in FIG. 5.

As is evident from FIGS. 1 through 5, if the means of obstructing the passage of developer according to the method of this invention is provided on the chromatography medium, not only the symbol (+) but also (Y) and (N) or other complex geometric symbols appear clearly.

The foregoing general discussion and experimental examples are intended to be illustrative of the present invention, and are not to be considered limiting. Other variations within the spirit and scope of this invention are possible and will present themselves to those skilled in the art.

I claim:

1. A method for detecting the presence of a specific analyte in solution comprising the steps of:
    affixing to an elongated chromatographic medium having a longitudinal axis a first antibody which binds with specificity to said analyte, said first antibody disposed on said chromatographic medium in a pattern which forms a predetermined geometric symbol or symbols consisting of a plurality of line segments, said line segments including a first line segment substantially parallel to said longitudinal axis and a second line segment substantially perpendicular to said longitudinal axis;
    partially blocking or obstructing the expected passage of a moving phase or solvent using at least one partial obstruction to direct said moving phase or solvent through said symbol or symbols on said chromatographic medium in a direction other than parallel to said longitudinal axis, wherein said at least one partial obstruction is positioned immediately upstream or immediately downstream or lateral to said predetermined geometric symbol or symbols;
    reacting said solution to a marker-second antibody complex which binds with specificity to said analyte to form analyte-marker-second antibody complexes in the presence of said analyte;
    eluting said solution containing any said analyte-marker-second antibody complex around said at least one partial obstruction; and;
    observing the substantially complete formation, or lack thereof, of the predetermined geometric symbol or symbols by means of said marker.

2. The method of claim 1 wherein at least one said partial obstruction is positioned immediately upstream of said predetermined geometric symbol or symbols.

3. The method of claim 1 wherein at least one said partial obstruction is positioned lateral to said predetermined geometric symbol or symbols.

4. The method of claim 1 wherein at least one said partial obstruction is positioned immediately downstream of said predetermined geometric symbol or symbols.

5. The method of claim 1 wherein at least one said partial obstruction is formed by means of removing a portion or portions of said medium by notching, punching or cutting said medium.

6. The method of claim 1 wherein at least one said partial obstruction is formed by means of physically affixing a hydrophobic blocking agent to said medium.

7. The method of claim 6 wherein said agent is a hydrophobic polymer.

8. The method of claim 7 wherein said polymer is an oil-based ink.

9. The method of claim 1 wherein at least one said partial obstruction is positioned at a lateral edge of said medium.

10. The method of claim 5 wherein said portion or portions removed are in a shape taken from the group comprising rectangles, half-circles and triangles.

11. The method of claim 6 wherein said blocking agent is applied in a shape taken from the group comprising rectangles, half-circles and triangles.

12. The method of claim 1 wherein said marker is taken from the group comprising colloidal gold particles, colored latex and insoluble dye polymers.

13. The method of claim 1 wherein said medium is taken from the group comprising glass filters, nitrocellulose and nylon.

14. The method of claim 1 wherein said first antibody is affixed by means of direct printing an aqueous solution.

15. The method of claim 1 wherein said first antibody is affixed by means of printing with latex to which the first antibody is bonded.

16. The method of claim 1 wherein said marker-second antibody is affixed to said medium upstream from said symbol so that the elution of a solution potentially containing said analyte will pass through and form an analyte-marker second antibody complex prior to reaching said symbol.

* * * * *